United States Patent
Nakamura et al.

(10) Patent No.: US 6,696,301 B2
(45) Date of Patent: Feb. 24, 2004

(54) METHOD FOR DETERMINATION OF 5-HYDROXYCREATININE

(75) Inventors: Ko Nakamura, Hyogo (JP); Katsumi Kawano, Tokyo (JP)

(73) Assignee: Nippon Zoki Pharmaceutical Co., Ltd., Osaka (JP)

( * ) Notice: Subject to any disclaimer, the term of this patent is extended or adjusted under 35 U.S.C. 154(b) by 253 days.

(21) Appl. No.: 09/968,823

(22) Filed: Oct. 2, 2001

(65) Prior Publication Data

US 2002/0137224 A1 Sep. 26, 2002

(30) Foreign Application Priority Data

Oct. 3, 2000 (JP) ........................................ 2000-303172

(51) Int. Cl.$^7$ ............................................... G01N 33/00
(52) U.S. Cl. ................. 436/106; 436/161; 436/177; 436/178; 436/811; 436/815; 210/656; 210/660; 210/662
(58) Field of Search ................. 436/106, 177, 436/178, 161, 811, 815; 210/656, 662, 660

(56) References Cited

FOREIGN PATENT DOCUMENTS

| JP | 04-161854 | 6/1992 |
| JP | 05-119038 | 5/1993 |
| JP | 6023279 | 2/1994 |
| JP | 2000-352564 | 12/2000 |

OTHER PUBLICATIONS

Chem. Abst. 101:106722 XP–002190360—Higashidate, Sakae et al., "Rapid and highly sensitive method for the determination of quanidino compounds in body fluids", Bunseki Kagaku (1984), 33(7), 366–70.

Higashidate et al., *Bunseki Kagaku*, 33, (1984), pp. 366–370.

Nakamura et al., "Creatol, a Creatinine Metabolite, as a Useful Determinant of Renal Function," *Nephron* 1994, 66:140–146.

*Primary Examiner*—Jill Warden
*Assistant Examiner*—Monique T. Cole
(74) *Attorney, Agent, or Firm*—Hollander Law Firm, P.L.C.

(57) ABSTRACT

The present invention provides a highly sensitive and practical method for the determination of and the separation of 5-hydroxycreatinine from a sample of bodily fluid. The method of the present invention is useful as a method for the testing of renal dysfunction, such as uremia, chronic nephritis and closure of the urinary tract, etc. A separation solvent of pH 4.1 to 4.6 is used in a high performance liquid chromatography step that is carried out using a strongly acidic cation-exchange resin, such as a styrene-divinylbenzene resin. The determination sensitivity is a concentration of only about 0.02 $\mu$M, whereby 5-hydroxycreatinine in blood of healthy persons can be determined for the first time. Moreover, only one separation solvent, such as a citrate, need be used and the cycle time for analysis is only about 14 minutes per measurement. Thus, a practitioner using one set of HPLC equipment is able to carry out about 100 determinations per day.

22 Claims, 2 Drawing Sheets

METHOD FOR DETERMINATION OF 5-HYDROXYCREATININE

FIELD OF THE INVENTION

The present invention relates to a method for determining 5-hydroxycreatinine, which method is useful as a test for renal function disorders, uremia, chronic nephritis, and closure of the urinary tract, etc.

BACKGROUND OF THE INVENTION

5-Hydroxycreatinine has been found to be an intermediate in the production of methylguanidine, which is a primary urinary toxin accumulated in blood of patients suffering from renal failure. It has been clarified that 5-hydroxycreatinine is produced by a nonenzymatic oxidation of creatinine. Using conventional determination methods, 5-hydroxycreatinine is not detected in the sera of healthy persons, but it is detected in the sera of renal failure patients starting in the initial stage of renal failure and increasing as the symptoms worsen. Therefore, 5-hydroxycreatinine has drawn attention as a marker for renal function disorder and its determination is considered to be an important tool for the evaluation of the disease condition and for early diagnosis of patients suffering from renal failure.

It is believed that an hydroxy radical having a very high reactivity participates in the nonenzymatic oxidation of creatinine. Accordingly, 5-hydroxycreatinine, an intermediate in the reaction of conversion of creatinine to methylguanidine, gets much attention not only as a precursor of methylguanidine, a urinary toxin, but also as an index for the production of hydroxy radical in vivo (an index for oxidative stress state). It has therefore been suggested at present that the determination of 5-hydroxycreatinine is useful as a marker for renal function disorders such as renal failure, diabetic nephropathy and nephritis and also as a marker for systemic oxidative stress.

Known methods for determining 5-hydroxycreatinine as a marker for renal disorder include a method using a high performance liquid chromatography (HPLC) by Nakamura, one of the present inventors (Japanese Patent Laid-Open Nos. 04/161854 and 05/119038). In this method, 5-hydroxycreatinine is separated from blood, serum or urine by a high performance liquid chromatography and the resulting 5-hydroxycreatinine is hydrolyzed and converted to methylguanidine. Methylguanidine is then subject to a quantitative determination by means of fluorescent labeling.

In the method described in the above-mentioned laid-open patent gazettes, separation of 5-hydroxycreatinine from blood, serum or urine is carried out using a column of cation-exchange resin which method requires the application of five kinds of separation solvents, in accordance with the method of Higashidate, et al. (Bunseki Kagaku, 33, pages 366–370 (1984)). In this method, the first separation solvent (sodium citrate/hydrochloric acid; pH 3.00) is eluted for 4.5 minutes; the second separation solvent (sodium citrate/hydrochloric acid; pH 3.50) is eluted for 2.8 minutes; the third separation solvent (sodium citrate/hydrochloric acid; pH 5.25) is eluted for 2.4 minutes; the fourth separation solvent (sodium citrate/boric acid/sodium hydroxide; pH 10.00) is eluted for 2.3 minutes; and the fifth separation solvent (1M sodium hydroxide) is eluted for 30 minutes.

The separating method described in the above-mentioned laid-open patent gazettes correlates with the Higashidate et al method, so it is necessary to prepare as many as five types of separation solvents prior to performing a determination. A complex determination process results which requires much labor, such as programming for switching the separation solvents and for control of eluting time. Moreover, the sensitivity of the determination is 0.5–1 nmol/mL (6.5–13 μg/dL) which is not sufficient for the measurement of changes in small amounts of 5-hydroxycreatinine in the samples of living organisms.

Also disclosed in a paper by Nakamura, et al. (Nephron, 66, pages 140–146 (1994)) is a method for separating and determining 5-hydroxycreatinine using a separation solvent prepared by addition of 1 part of dimethyl sulfoxide (DMSO) to 9 parts of 0.4M citric acid to adjust the pH to 5.25. In the method according to the Nakamura, et al. paper, the eluting time is as long as 30 minutes, which is an inefficient method. Further, the sensitivity for the measurement is about 2 μg/dL, which is still insufficient for measuring the changes in small amounts of 5-hydroxycreatinine in or before the initial stage of renal dysfunction. Accordingly, this method is unsatisfactory as well.

In addition, Nakamura et al., in Japanese Patent Publication No. JP 2000 352564, disclose the determination of 5-hydroxycreatinine via the conversion of 5-hydroxycreatinine to methylguanidine prior to fluorescence spectroscopy. The conversion to methylguanidine may be achieved by raising the temperature of a sample containing the 5-hydroxycreatinine in boric acid or in a boric acid solution to hydrolyze the 5-hydroxycreatinine. A ninhydrin method may be used for labeling of the methylguanidine with fluorescence. The pH of the reaction solution obtained by labelling the methylguadinine with fluorescence is adjusted before the high-speed liquid chromatography.

The present inventors have carried out further intensive investigation and have found a method for the rapid determination of 5-hydroxycreatinine with unexpectedly superior sensitivity. The method of the present invention overcomes sensitivity problems, and overcomes the need for a high number of elution solvents and complex control of their elution times.

SUMMARY OF THE INVENTION

The present invention relates to a method for determining 5-hydroxycreatinine in a sample, wherein a separation solvent having a pH of about 4.1 to about 4.6 is selected for use in a high performance liquid chromatography (HPLC) step which is carried out with a strongly acidic cation-exchange resin medium. The present invention also comprises a method for separating 5-hydroxycreatinine contained in a sample by subjecting the sample to HPLC in a strongly acidic cation-exchange resin medium using a separation solvent having a pH of about 4.1 to about 4.6.

The present invention provides a highly sensitive and practical method for determining 5-hydroxycreatinine, which method is useful in testing for renal function disorders such as renal failure, diabetic nephropathy, nephritis, uremia, and closure of the urinary tract, and also for systemic oxidative stress. The method of the present invention comprises performing a high performance liquid chromatography to separate 5-hydroxycreatinine from bodily fluids, urine or other materials sampled from animals and from human beings.

Preferred embodiments of the present invention are:

(1) A method for determining 5-hydroxycreatinine comprising performing HPLC in a column or exchange resin medium comprising a strongly acidic cation-exchange resin, wherein a separation solvent having a pH of about 4.1 to about 4.6 is used;

(2) The method for determining 5-hydroxycreatinine according to the above method (1), wherein the strongly acidic cation-exchange resin is a sulfonic acid cation-exchange resin of the styrene-divinylbenzene series;

(3) The method for determining 5-hydroxycreatinine according to any of the above methods (1) or (2), wherein the separation solvent comprises a mixture of sodium citrate and dimethyl sulfoxide;

(4) The method for determining 5-hydroxycreatinine according to one of the above methods (1) to (3), wherein said 5-hydroxycreatinine is determined from bodily fluid or urine derived from animals;

(5) The method for determining 5-hydroxycreatinine according to the above method (4), wherein 5-hydroxycreatinine is determined from bodily fluid or urine derived from a human being;

(6) The method for determining 5-hydroxycreatinine according to the above methods (4) or (5), wherein 5-hydroxycreatinine is determined from blood;

(7) The method for determining 5-hydroxycreatinine according to the above method (6), wherein 5-hydroxycreatinine is determined from serum; and (8) The method for determining 5-hydroxycreatinine according to the above methods (4) or (5), wherein 5-hydroxycreatinine is determined from urine.

(9) A method for separating 5-hydroxycreatinine comprising subjecting a sample containing 5-hydroxycreatinine to HPLC in a strongly acidic cation-exchange resin medium using a separation solvent having a pH of about 4.1 to about 4.6.

DETAILED DESCRIPTION OF THE INVENTION

Figure 1:
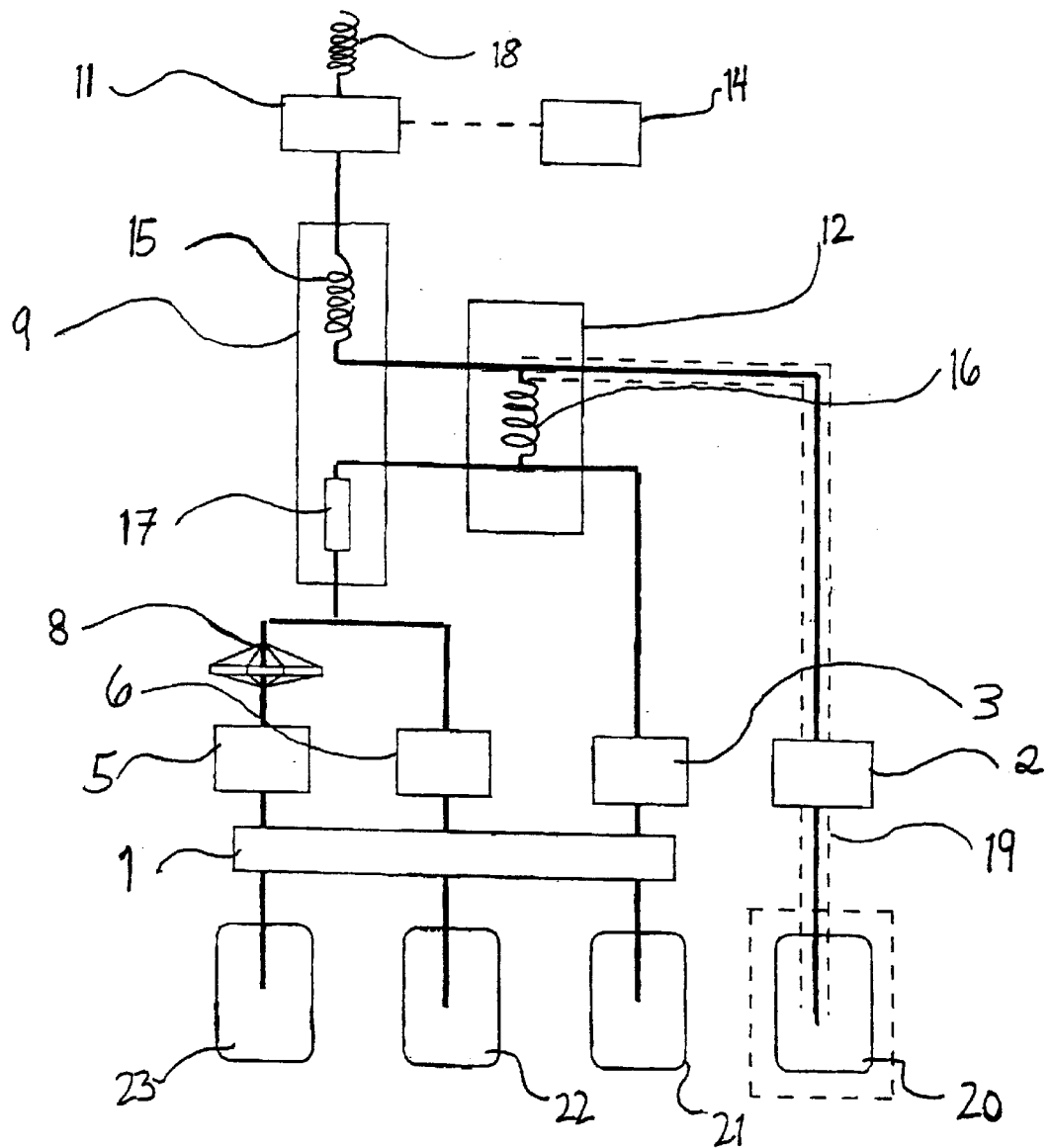
FIG. 1 depicts an outline of constituent parts of an apparatus for practicing the determination method of the present invention.

The present invention relates to a method for determining 5-hydroxycreatinine comprising high performance liquid chromatography (HPLC), wherein a separation solvent having a pH of about 4.1 to about 4.6 is selected and applied to a column comprising a strongly acidic cation-exchange resin to separate or elute 5-hydroxycreatinine from the column. In embodiments of the invention, a sample such as a bodily fluid, such as urine or serum, is subjected to protein removal using known techniques such as denaturization or precipitation, and centrifugation or filtration. In preferred embodiments, proteins may be removed by admixing a sample with trichloroacetic acid. The resulting mixture or sample is very acidic and may be injected as is into the column. It is not necessary to adjust the pH of the body fluid sample to pH 4.1 to 4.6. Use of a strongly acidic cation exchange resin results in elution of the acids in the sample and retention in the column or attachment to the column of substances such as 5-hydroxycreatinine. Subsequently, a separation solvent having a pH of about 4.1 to about 4.6 is pumped into or caused to flow through the column to separate and remove or elute sample components, such as 5-hydroxycreatinine which were attached to the column. The column may be regenerated for use in subsequent determinations by injection of and elution with an alkaline solvent or base such as 1N NaOH.

The strongly acidic cation-exchange resin used in the present invention may preferably be a sulfonic acid cation-exchange resin selected from the group consisting of styrene-divinylbenzene resins. Thus, the cation-exchange resin employed is preferably a strongly acidic cation-exchange resin having a sulfonic acid group introduced into a styrene-divinylbenzene copolymer. Various kinds of sulfonic acid functional styrene-divinylbenzene resins have been made commercially available, and may be employed herein, for example, Guanidino Pack II (trade name) made by Nippon Bunko K. K.

Separation solvents or elution solvents used in the HPLC method for determining 5-hydroxycreatinine according to the present invention may include citrate buffers, phosphate buffers, etc. Citrate buffers are preferably used in the present invention and can be prepared using sodium citrate, potassium citrate, etc. When sodium citrate is used, a solution concentration of 0.30–0.45M in terms of sodium ion concentration is preferred. To obtain a high separating ability for achieving the object of the present invention, it is preferred to use a mixed separation solvent of sodium citrate/dimethyl sulfoxide, which is a mixed solvent where dimethyl sulfoxide (DMSO) is added in appropriate amounts to a citrate buffer. Preferred effects, such as an increase in fluorescence intensity and good separation of each elution peak, may be obtained by addition of dimethyl sulfoxide (DMSO). The proportion of DMSO mixed with a buffer such as a citrate buffer may range from about 1% to about 20%, by volume, preferably from about 5% to about 15%, by volume, and most preferably about 10%, by volume, based upon the total volume of the mixed solvent of buffer and DMSO.

The pH of the separation solvent may be within a range of from about 4.1 to about 4.6, preferably from about 4.2 to about 4.3, and may be adjusted by addition of an acid, such as hydrochloric acid, to the above-mentioned separation solvent. A solvent having a constant pH may be used during HPLC, that is, it is not necessary to adjust the pH of the separation solvent during HPLC. In the determination of 5-hydroxycreatinine in samples derived from animals, such as human urine and serum, it is necessary to select a pH whereby 5-hydroxycreatinine is most distinctly separated from other contaminants. As will be apparent from the experimental results mentioned below and shown in FIG. 2, it is preferred to use a separation solvent having a pH of about 4.2 to about 4.3 so that big peaks representing contaminants are eluted before and after the elution of 5-hydroxycreatinine.

Substrates or samples useful for determining 5-hydroxycreatinine in the present invention may include bodily fluid or urine derived from animals, such as blood, serum, plasma and urine. Preferable substrates or samples may include the blood, serum, plasma, urine, etc. derived from human beings. These substrates can be used as items for clinical testing.

Preferred embodiments of the present invention are:

(1) A method for determining 5-hydroxycreatinine comprising performing high performance liquid chromatography, wherein a separation solvent having a pH of 4.1 to 4.6 is applied to a column or exchange resin medium comprising a strongly acidic cation-exchange resin;

(2) The method for determining 5-hydroxycreatinine according to the above method (1), wherein the strongly acidic cation-exchange resin is a sulfonic acid cation-exchange resin of the styrene-divinylbenzene series;

(3) The method for determining 5-hydroxycreatinine according to any of the above methods (1) or (2), wherein the separation solvent comprises a mixture of sodium citrate and dimethyl sulfoxide;

(4) The method for determining 5-hydroxycreatinine according to one of the above methods (1) to (3), wherein said 5-hydroxycreatinine is determined from the bodily fluid or urine derived from animals;

(5) The method for determining 5-hydroxycreatinine according to the above method (4), wherein 5-hydroxycreatinine is determined from the bodily fluid or urine derived from a human being;

(6) The method for determining 5-hydroxycreatinine according to the above methods (4) or (5), wherein 5-hydroxycreatinine is determined from blood;

(7) The method for determining 5-hydroxycreatinine according to the above method (6), wherein 5-hydroxycreatinine is determined from serum; and (8) The method for determining 5-hydroxycreatinine according to the above methods (4) or (5), wherein 5-hydroxycreatinine is determined from urine.

(9) A method for separating 5-hydroxycreatinine comprising subjecting a sample containing 5-hydroxycreatinine to HPLC in a strongly acidic cation-exchange resin medium using a separation solvent having a pH of about 4.1 to about 4.6.

The present invention will now be more specifically illustrated by way of the following non-limiting examples wherein all parts, percentages, and ratios are by weight, all temperatures are in ° C., and all pressures are atmospheric unless otherwise indicated:

EXAMPLES

In the following experiments, the system employed and the method of use of the system is shown in FIG. 1 and is explained in detail below:

As shown in FIG. 1, in determining 5-hydroxycreatinine in an analyte sample or substrate, the separation solvent having a desired pH and 1N NaOH, are fed through a degassing unit, such as a GL Sciences Model 546B degassing unit 1 via separate pumps 5 and 6, respectively. Pumps 5 and 6 may comprise a Shimadzu Model LC-6AD. The substrate itself (e.g. urine) which has been subjected to a protein removal step is contained in the auto-injector or autosampler 8. Protein removal from the substrate may be carried out using known methods, such as by adding trichloroacetic acid to the substrate.

To begin HPLC, the trichloroacetic acid treated sample is injected into column 17 by auto-sampler 8. The acids in the sample are eluted and substances such as 5-hydroxycreatinine are attached to the strongly acidic cation exchange resin in column 17. Then, a separation solvent having a pH of 4.1 to 4.6 pumped from reservoir 23 may be injected into column 17 to elute the substrate fluid, e.g. blood, by autosampler 8. Throughout HPLC, autosampler 8 meters into column 17 the separation solvent to elute the substrate fluid. The autosampler 8 may comprise a Shimadzu Model SIL-6B auto-injector.

During HPLC, the prepared samples are eluted through column 17 to purify and separate the various components of the substrate fluid, including 5-hydroxycreatinine. A strongly acidic cation-exchange resin, Guanidino Pack II (manufactured by Nippon Bunko K. K.) is used in these Examples. Guanidino Pack II is a column 17 having a size of 6.0 mm (ø)×35.0 mm, and represents a preferred embodiment of the present invention. Column 17 is contained in an oven/reactor 9, such as a Shimadzu Model CTO-6A, which is kept at 65° C. The desired column fraction is then fed to a hydrolysis reactor 12 which is kept at 120° C.

Once a separation in column 17 is completed by HPLC, column 17 may be regenerated by a base, e.g. 1N NaOH, that is pumped into column 17 from reservoir 22.

Separately from HPLC and while HPLC is being performed, the PQ (9,10-phenanthrenequinone) reagent pumped from reservoir 20, or, alternatively, another fluorescence labelling reagent such as ninhydrin or benzoin, is stored in an atmosphere protected by a shielding light 19 and pumped via pump 2 into the hydrolysis reactor 12. The PQ reagent may be obtained by dissolving 9,10-phenanthrenequinone in DMF. Pump 2 may comprise a Nihon Bunko Model 880-PU pump. The hydrolysis reactor 12, which may be a TOSOH Model RE-8010, comprises a hydrolysis reaction coil 16 which mixes fluids for reaction.

At the same time as the labelling reagent and the desired column fraction are fed to hydrolysis reactor 12, 2N NaOH pumped from reservoir 21 is fed through degasser 1 via pump 3 and into the hydrolysis reactor 12. Pump 3 may be the same type of pump as pump 2.

In the hydrolysis reactor 12, a column fraction containing 5-hydroxycreatinine is reacted at 120° C. with 2N NaOH to form methylguanidine. The methylguanidine is labelled preferentially by the PQ reagent when it is fed into reactor 9 at reaction coil 15, which is kept at 65° C.

Finally, labelled methylguanidine is fed into a spectrofluorometer 11, which may be a Shimadzu Model RF-10A-XL and/or a Hitachi F-1050 model machine. The data is analyzed by a data processor 14, such as a Shimadzu Model C-R4A and can be printed out on a printer (not shown) such as a Shimadzu printer. A reaction coil 18 lying downstream of spectrofluorometer 11 minimizes back pressure in the system.

The system may be controlled by a system controller (not shown), which may be a Shimadzu SCL-6B device, and a power control unit (not shown), such as a device manufactured by Shimadzu, all of which are known commercially available devices.

Example 1

Investigation: Effect of Varying pH on Eluting Time of 5-hydroxycreatinine

In a strongly acidic cation-exchange resin, eluting time for the analyte substance varies mostly depending upon the ion concentration and the pH. Therefore, the amount of hydrochloric acid added to the separation solvent (a mixed solvent comprising 9 parts, by volume, of 0.4M sodium citrate solution and 1 part, by volume, of DMSO) was varied to change the pH. For each pH level, e.g. 4.3, a full elution of an analyte substance is completed using a single separation solvent having the given pH level. The resulting change in an eluting pattern for 5-hydroxycreatinine was monitored over the elution of several samples, each sample being fully eluted at a different pH.

(1) Method

Urine was sampled from a healthy person, and the proteins were removed therefrom by known methods, e.g. trichloroacetic acid addition, to give a sample. The amount of hydrochloric acid added to the separation solvent was varied from elution to elution, so that pH was changed within a range of 3–5 to give eluents. Switching to a 1 N sodium hydroxide was not carried out. Only a separation solvent containing a varied proportion of hydrochloric acid was used. Symbols g1 to g7 (FIG. 2) were assigned to the peaks of contaminants other than the peak of 5-hydroxycreatinine and the behavior of those peaks was monitored.

(2) Result

Figure 2:
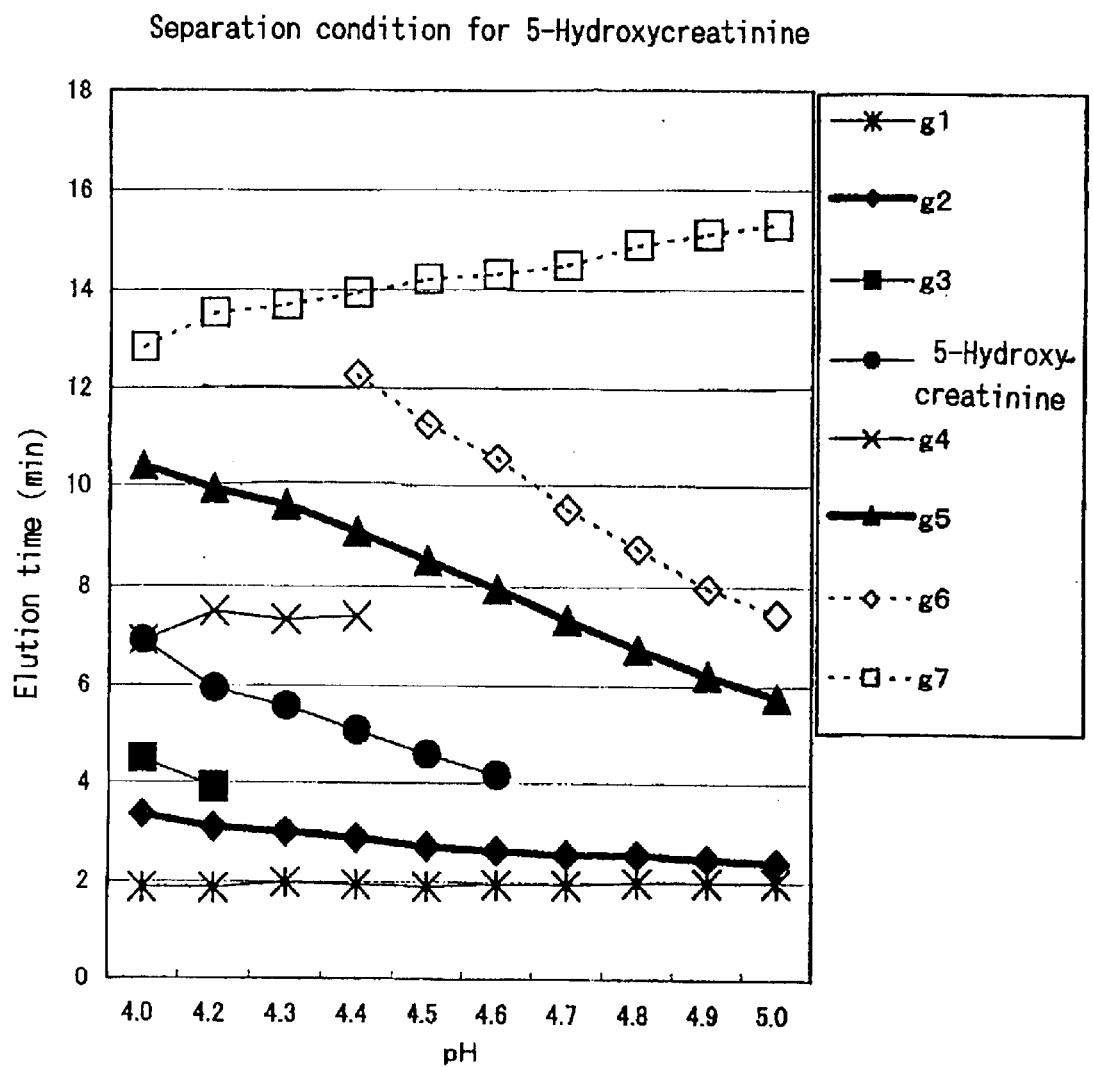
FIG. 2 depicts a graph of the elution time of 5-hydroxycreatinine and other contaminants in the urine of a healthy person on the ordinate (y-axis) versus a change in the pH of the separation solvent on the abscissa (x-axis).

The results of varying pH from 4–5 is shown in FIG. 2. Bold lines in the drawing denote big peaks. There were two types of peaks: In one, the higher the pH, the quicker the eluting time; in another, there was almost no change in eluting time as pH was raised. The result of this experiment showed that the peak of 5-hydroxycreatinine and those of other contaminants were separated to the biggest extent at about pH 3.6 and about pH 4.3. However, the eluting time for 5-hydroxycreatinine was quicker at pH 4.3, and that was believed to be practical and preferred. Accordingly, a separation solvent adjusted to pH 4.3 was used in the following experiments.

Example 2

Stability of Calibration Curve of 5-hydroxycreatinine and its Detecting Limit (1) Method A 5-hydroxycreatinine sample was diluted with 10% trichloroacetic acid (TCA) to make sample aliquots containing 20, 10, 4, 2, 1, 0.4, 0.2 and 0 $\mu$M 5-hydroxycreatinine. The amount for infusion was made 0.1 mL for each sample aliquot. Each of the diluted samples was repeatedly measured and the stability of the calibration curve was checked. A range in which the coefficient of variation (CV), defined as the standard deviation (SD) divided by the mean intensity of a measured peak, multiplied by 100%, was less than 20% was adopted as measurable range.

(2) Result

The results are shown in Table 1:

TABLE 1

Stability of a Calibration Curve of 5-Hydroxycreatinine (Number of Samples Tested) vs. 5-Hydroxycreatinine ($\mu$M) (Horizontal Axis)

|  | 20 | 10 | 4 | 2 | 1 | 0.4 | 0.2 | 0 |
|---|---|---|---|---|---|---|---|---|
| 1 | 418697 | 211172 | 85131 | 42890 | 21109 | 8462 | 4479 | 0 |
| 2 | 421971 | 217147 | 86989 | 43408 | 21400 | 8875 | 4557 | 0 |
| 3 | 445784 | 221821 | 88146 | 44617 | 21807 | 8716 | 4621 | 0 |
| 4 | 443129 | 217290 | 88665 | 44591 | 22250 | 8824 | 4540 | 0 |
| 5 | 441884 | 216756 | 90541 | 44652 | 22089 | 9279 | 4250 | 0 |
| 6 | 438391 | 223424 | 88563 | 43400 | 21709 | 8638 | 4448 | 0 |
| 7 | 438945 | 225801 | 91510 | 43480 | 22561 | 9202 | 4732 | 0 |
| mean | 435543.0 | 219058.7 | 88506.4 | 43862.6 | 21846.4 | 8856.6 | 4516.9 | 0 |
| SD | 10726.2 | 4940.1 | 2121.9 | 734.4 | 499.3 | 295.1 | 148.8 | 0 |
| CV | 2.46 | 2.26 | 2.40 | 1.67 | 2.29 | 3.33 | 3.29 | — |

In the method of the present invention, even at the infusion rate of 20 pM/0.1 mL (0.2 $\mu$M), the determination was so stable that the CV of the read values was less than 20%. It is likely that stable data will be available at far lower concentrations of the analyte.

Example 3

Stability of a Calibration Curve of 5-hydroxycreatinine and its Detection Limit at Lower Concentration Range (1) Method 5-hydroxycreatinine samples were diluted with 10% TCA to make 2, 0.8, 0.4, 0.2, 0.08, 0.04, 0.02 and 0 $\mu$M sample aliquots. The amount for infusion was made 0.1 mL for each sample aliquot. Each of the diluted samples was repeatedly measured and the stability of the calibration curve was checked. A range in which the coefficient of variation (CV) was less than 20% was adopted as a measurable range.

(2) Result

The results are shown in Table 2:

TABLE 2

Stability of a Calibration Curve of 5-Hydroxycreatinine (Number of Samples Tested) vs. 5-Hydroxycreatinine ($\mu$M) (Horizontal Axis)

|  | 2 | 0.8 | 0.4 | 0.2 | 0.08 | 0.04 | 0.02 | 0 |
|---|---|---|---|---|---|---|---|---|
| 1 | 64393 | 25202 | 11968 | 5784 | 2284 | 1009 | 605 | 0 |
| 2 | 59977 | 24426 | 12047 | 5582 | 2325 | 1049 | 640 | 0 |

TABLE 2-continued

Stability of a Calibration Curve of 5-Hydroxycreatinine (Number of Samples Tested) vs. 5-Hydroxycreatinine ($\mu$M) (Horizontal Axis)

|  | 2 | 0.8 | 0.4 | 0.2 | 0.08 | 0.04 | 0.02 | 0 |
|---|---|---|---|---|---|---|---|---|
| 3 | 63323 | 24931 | 12542 | 5663 | 1990 | 1185 | 772 | 0 |
| 4 | 62254 | 26640 | 11767 | 6173 | 2374 | 1113 | 961 | 0 |
| 5 | 63071 | 23647 | 11717 | 6437 | 2708 | 1434 | 796 | 0 |
| mean | 62603.6 | 24969.2 | 12008.2 | 5927.8 | 2336.2 | 1158.0 | 754.8 | 0 |
| SD | 1655.2 | 1105.7 | 328.3 | 363.9 | 256.1 | 168.1 | 141.5 | 0 |
| CV | 2.64 | 4.43 | 2.73 | 6.14 | 10.96 | 14.52 | 18.75 | — |

As shown in Table 2, it was found that the determination of a table CV of less than 20% was available at a concentration of 0.02 $\mu$M of the analyte. The calibration curve by means of a least-squares method showed a good linearity as follows:

$$y=31339x-147.63\ R^2=0.9988$$

The y intercept is −147.63 and it was about ⅕ of the read value for 0.02 $\mu$M which was within an allowable error range from 1SD.

Example 4

Investigation of Sensitivity in Measurement

From the results of the above Examples 2 and 3, the measurable range of the method of determination according to the present invention was 0.02–20 $\mu$M (infusion of 2 pM to 2 nM/0.1 mL). In addition, the calibration curve showed a good linearity from the maximum measuring concentration of 20 $\mu$M to the minimum measuring concentration of 0.02 $\mu$M or even to zero concentration. Even if a calibration curve where samples in fine dilution series are arranged, i.e. aliquotted, is not prepared, due to the linearity of the calibration curve, it is possible to prepare a calibration curve by means of a one-point absolute determination method at 20 $\mu$M. Further, when 5-hydroxycreatinine levels in the sera of healthy persons are considered, it is likely that nearly all samples taken from such persons will be within a measurable range of concentration because the determination sensitivity is so low (about 0.02 $\mu$M). With regard to the samples having concentrations of 20 $\mu$M or more, determination is possible when subjected to determination after dilution.

As will be apparent from the above results, the determination sensitivity in the method for determining 5-hydroxycreatinine according to the present invention is 0.02 $\mu$M (0.26 $\mu$g/dL), whereby 5-hydroxycreatinine even in blood of healthy persons can be determined. Accordingly, the method of the instant invention provides a very highly sensitive determination method as compared with conventional methods. Moreover, according to the determination method of the present invention, only one separation solvent may be used. Still further, a cycle of the time for analysis may be about 14 minutes per measurement, which is quicker than the conventional methods. Thus, a practitioner using one set of HPLC equipment may be able to carry out about 100 determinations per day. When compared with the method described in the above-mentioned report by Nakamura, et al., about twice the treating ability and significantly higher sensitivity have been achieved.

The reason for the high sensitivity of the method according to the present invention is that because the separation solvent is in a more acidic region, 5-hydroxycreatinine is hardly decomposed during the analysis. As such, the method for determination of 5-hydroxycreatinine according to the present invention is a very efficient and useful determination method. Previously, a practical application of 5-hydroxycreatinine determination has been impossible and can now be achieved according to the method of the instant invention.

We claim:

1. A method for determining 5-hydroxycreatinine comprising subjecting a sample to high performance liquid chromatography (HPLC) in a strongly acidic cation-exchange resin medium using a separation solvent having a pH of about 4.1 to about 4.6.

2. A method for determining 5-hydroxycreatinine according to claim 1 wherein the strongly acidic cation-exchange resin is a sulfonic acid cation-exchange resin selected from the group consisting of styrene-divinylbenzene resins.

3. A method for determining 5-hydroxycreatinine according to claim 1, wherein the separation solvent comprises a mixture of sodium citrate and dimethyl sulfoxide.

4. A method for determining 5-hydroxycreatinine according to claim 2, wherein the separation solvent comprises a mixture of sodium citrate and dimethyl sulfoxide.

5. A method for determining 5-hydroxycreatinine according to claim 1, wherein said 5-hydroxycreatinine is determined from bodily fluid derived from an animal.

6. A method for determining 5-hydroxycreatinine according to claim 2, wherein said 5-hydroxycreatinine is determined from bodily fluid derived from an animal.

7. A method for determining 5-hydroxycreatinine according to claim 3, wherein said 5-hydroxycreatinine is determined from bodily fluid derived from an animal.

8. A method for determining 5-hydroxycreatinine according to claim 5, wherein 5-hydroxycreatinine is determined from bodily fluid derived from a human being.

9. A method for determining 5-hydroxycreatinine according to claim 6, wherein 5-hydroxycreatinine is determined from bodily fluid derived from a human being.

10. A method for determining 5-hydroxycreatinine according to claim 7, wherein 5-hydroxycreatinine is determined from bodily fluid derived from a human being.

11. A method for determining 5-hydroxycreatinine according to claim 5, wherein 5-hydroxycreatinine is determined from blood or serum.

12. A method for determining 5-hydroxycreatinine according to claim 6, wherein 5-hydroxycreatinine is determined from blood or serum.

13. A method for determining 5-hydroxycreatinine according to claim 7, wherein 5-hydroxycreatinine is determined from blood or serum.

14. A method for determining 5-hydroxycreatinine according to claim 1, wherein said separation solvent comprises a buffer and dimethylsulfoxide and the amount of dimethylsulfoxide is from about 1% by volume to about 20% by volume, based upon the total volume of the buffer and dimethylsulfoxide.

15. A method for determining 5-hydroxycreatinine according to claim 4, wherein said separation solvent mixture comprises 9 parts, by volume, of sodium citrate buffer and 1 part, by volume, of dimethylsulfoxide.

16. A method for determining 5-hydroxycreatinine according to claim 1, wherein said separation solvent is adjusted to a pH of about 4.2 to about 4.3.

17. A method for determining 5-hydroxycreatinine according to claim 1 wherein 5-hydroxycreatinine is determined from human blood, serum, plasma, or urine.

18. A method for determining 5-hydroxycreatinine according to claim 17, wherein the sensitivity of the determination is about 0.02 $\mu$M 5-hydroxycreatinine.

19. A method for determining 5-hydroxycreatinine according to claim 17, wherein eluted 5-hydroxycreatinine is hydrolyzed to methylguanidine, the methylguanidine is labelled with a fluorescence labelling reagent to obtain labelled methylguanidine, and the labelled methylguanidine is detected in a spectrofluorometer for the quantitative determination of 5-hydroxycreatinine.

20. A method for determination of a renal function disorder or systemic oxidative stress comprising subjecting a bodily fluid sample to high performance liquid chromatography (HPLC) in a strongly acidic cation-exchange resin medium using a separation solvent having a pH of about 4.1 to about 4.6 to elute 5-hydroxycreatinine, and determining the amount of eluted 5-hydroxycreatinine as a marker for renal function disorder or systemic oxidative stress.

21. A method according to claim 20 wherein 5-hydroxycreatinine is determined from human blood, serum, plasma, or urine.

22. A method for separating 5-hydroxycreatinine comprising subjecting a sample to high performance liquid chromatography (HPLC) in a strongly acidic cation-exchange resin medium using a separation solvent having a pH of about 4.1 to about 4.6.

* * * * *